United States Patent [19]

Inouye et al.

[11] 3,959,256

[45] May 25, 1976

[54] 9-O-ALKANOYL-3''-O-ALKANOYLOXYMETHYL-SF-837 SUBSTANCE AND THE PRODUCTION THEREOF

[75] Inventors: Shigeharu Inouye, Yokohama; Shoji Omoto, Tokyo; Katsuyoshi Iwamatsu, Zama; Taro Niida, Yokohama; Toyoaki Kawasaki, Tokyo; Takashi Tsuruoka, Kawasaki, all of Japan

[73] Assignee: Meiji Seika Kaisha, Ltd., Tokyo, Japan

[22] Filed: Sept. 12, 1974

[21] Appl. No.: 505,310

[52] U.S. Cl. .......................... 260/210 AB; 424/180
[51] Int. Cl.² ........................................ C07H 17/08
[58] Field of Search ........................... 260/210 AB

[56] References Cited
UNITED STATES PATENTS

| | | | |
|---|---|---|---|
| 3,792,035 | 2/1974 | Fukatsu et al. | 260/210 AB |
| 3,855,202 | 12/1974 | Omoto et al. | 260/210 AB |

*Primary Examiner*—Johnnie R. Brown
*Attorney, Agent, or Firm*—Larson, Taylor and Hinds

[57] ABSTRACT

A 9-O-alkanoyl-3''-O-alkanoyloxymethyl-SF-837 substance is now synthetized, which is a new compound useful in that this new 9-O-alkanoyl-3''-O-alkanoyloxymethyl derivative of the SF-837 substance exhibits an antibacterial activity comparable to that of the parent SF-837 substance but is advantageously free from the unpleasant bitter taste inherent to the SF-837 substance and is hence adapted for oral administration. A process of producing the 9-O-alkanoyl-3''-O-alkanoyloxymethyl-SF-837 substance is also provided, which comprises hydrolysing partially and selectively a 9,2'-di-O-alkanoyl-3''-O-alkanoyloxymethyl-SF-837 substance in an aqueous alkanol or aqueous acetone. The 9,2'-di-O-alkanoyl-3''-O-alkanopyloxymethyl-SF-837 substance may be prepared by reacting a 9,2'-di-alkanoyl- or O-mono-O-alkanoyl-3''-O-thiomethoxymethyl-SF-837 substance with an alkanoic anhydride which is exemplified by acetic anhydride or propionic anhydride in the specification.

12 Claims, No Drawings

9-O-ALKANOYL-3''-O-ALKANOYLOXYMETHYL-SF-837 SUBSTANCE AND THE PRODUCTION THEREOF

This invention relates to a 9-O-alkanoyl-3''-O-alkanoyloxymethyl-SF-837 substance which is a new derivative of the antibiotic SF-837 substance and which is useful in therapeutic treatment of infections by gram-negative and gram-positive bacteria and is advantageously free from the unpleasant bitter taste of the parent antibiotic SF-837 substance itself. This invention further relates to a process for the production of such a 9-O-alkanoyl-3''-O-alkanoyloxymethyl-SF-837 substance.

The antibiotic SF-837 substance is a known useful macrolide antibiotic which is produced by a microorganism Streptomyces mycarofaciens as described in British patent No. 1,303,842. SF-837 substance is a compound which contains three hydroxyl groups in the 9-, 2'- and 3''-positions of the molecule and may be represented by the following formula:

[Chemical structure formula (I)]

as stated in the "Journal of Antibiotics" Vol. 24, page 460 (1971). The 9-hydroxyl group and 2'-hydroxyl group of the SF-837 substance molecule are relatively reactive while the tertiary 3''-hydroxyl group thereof is less reactive. The 9,2'-di-acetyl-SF-837 substance is shown in the British patent No. 1,303,842, and the 9-mono-acyl-SF-837 substance is described in British patent No. 1,325,943 and No. 1,358,114. Although the SF-837 substance itself as well as the 9,2'-di-acetyl derivative and the 9-mono-acyl derivative thereof are useful as an agent of treating therapeutically bacterial infections, these compounds suffer from such a disadvantage that they exhibit a long-lasting bitter taste characteristic to the macrolide antibiotics and hence are not suitable to be formulated into a liquid preparation which is intended to be given orally to infants who are often able to swallow the tablet or capsule preparations.

An object of this invention is to provide such a new acyl derivative of the SF-837 substance which exhibits an improved therapeutic effect in the treatment of the bacterial infections, as compared to the SF-837 substance itself and also is substantially free from the unfavorable bitter taste. The other object of this invention is to provide such a 9-O-alkanoyl-3''-O-alkanoyloxymethyl-SF-837 substance which shows the above-mentioned favorable properties. Further object of this invention is to provide a process for the production of the 9-O-alkanoyl-3''-O-alkanoyloxymethyl-SF-837 substance which is carried out in a facile way and with a high efficiency. Another objects of this invention will be clear from the following descriptions.

We succeeded in synthetizing a 9,2'-di-O-alkanoyl-3''-O-thiomethoxymethyl-SF-837 substance by reacting a 9,2'-di-O-alkanoyl-SF-837 substance with acetic anhydride and dimethylsulfoxide (see co-pending Japanese patent application No. 33897/72 which was pre-published under the Japanese patent application pre-publication No. 99188/73 laid open in December, 1973). We made further research on this thiomethoxymethylation reaction, and as a result we have now found that when a 9,2'-di-O-alkanoyl-SF-837 substance or 9-mono-O-alkanoyl-SF-837 substance is reacted with an excess of acetic anhydride and dimethylsulfoxide for a relatively long time of e.g. 5–7 days at ambient temperature or at an elevated temperature preferably in the presence of a small amount of carbon tetrachloride, there is formed the corresponding 9,2'-di-O-alkanoyl-3''-O-acetoxymethyl-SF-837 substance. We have also found that in this reaction there is formed as an intermediate product a 9,2'-di-O-alkanoyl-3''-O-thiomethoxymethyl-SF-837 substance and that when this intermediate product is further reacted with the acetic or propionic anhydride preferably in the presence of a small amount of dimethylsulfoxide, the 9,2'-di-O-alkanoyl-3''-O-acetoxymethyl-SF-837 substance or 9,2'-di-O-alkanoyl-3''-O-propionyloxymethyl-SF-837 substance is produced. We have further found that the 9,2'-di-O-alkanoyl-3''-O-thiomethoxymethyl-SF-837 substance formed as the intermediate product may be isolated and may be converted into its sulfoxide derivative by treating with 30% aqueous hydrogen peroxide and that this sulfoxide derivative may also be converted into the 9,2'-di-O-alkanoyl-3''-O-acetoxymethyl- or 9,2'-di-O-alkanoyl-3''-O-propionyloxymethyl-SF-837 substance by reacting with acetic or propionic anhydride preferably in the presence of a small amount of carbon tetrachloride. Moreover, we have now found that the 9,2'-di-O-alkanoyl-3''-O-alkanoyloxymethyl-SF-837 substance so obtained may partially be hydrolyzed into the corresponding 9-O-alkanoyl-3''-O-alkanoyloxymethyl-SF-837 substance with selective removal of the 2'-alkanoyl group therefrom, by treating with an aqueous acetone or an aqueous alkanol such as a lower alkanol of 1–4 carbon atoms, for example, methanol, ethanol, propanol or butanol containing a proportion of water. Thus, we have now succeeded in synthetizing 9-O-acetyl-3''-O-acetoxymethyl-SF-837 substance, 9-O-propionyl-3''-O-acetoxymethyl-SF-837 substance, 9-O-acetyl-3''-O-propionyloxymethyl-SF-837 substance and 9-O-propionyl-3''-O-propionyloxymethyl-SF-837 substance starting from the 9,2'-di-O-acetyl-SF-837 substance, 9,2'-di-O-propionyl-SF-837 substance, 9,0-acetyl-SF-837 substance or 9-O-propionyl-SF-837 substance. It has been found that these 9-O-alkanoyl-3''-O-alkanoyloxymethyl-SF-837 substances exhibit such a high antibacterial activity to gram-negative and gram-positive bacteria, as comparable to that of the parent SF-837 substance (free base) and give a higher curative effect than the parent SF-837 substance (the free base) when they are administered orally to mice which have intrapertioneally been infected with Staphylococcus aureus. In addition, these 9-O-alkanoyl-3''-O-alkanoyloxymethyl-SF-837 substances are practically free from the unpleasant long-lasting bitter taste characteristic to the parent SF-837 substance (the free base) and its 9,2'-di-O-acyl derivative.

According to a first aspect of this invention, therefore, there is provided as a new and useful compound a 9-O-alkanoyl-3''-O-alkanoyloxymethyl-SF-837 substance selected from 9-O-acetyl-3''-O-acetoxymethyl-SF-837 substance, 9-O-propionyl-3''-O-acetoxymethyl-SF-837 substance, 9-O-acetyl-3''-O-propionyloxymethyl-SF-837 substance and 9-O-propionyl-3''-O-propionyloxymethyl-SF-837 substance which are represented by the general formula (II):

wherein $R_1$ is acetyl or propionyl and $R_2$ is acetoxymethyl or propionyloxymethyl.

9-O-acetyl-3''-O-acetoxymethyl-SF-837 substance [in the general formula (II): $R_1$ = acetyl and $R_2$ = acetoxymethyl] is such a substance which has little bitter taste and is a colorless crystalline compound of a melting point of 174°–176°C (sintered) after the recrystallization from 75% aqueous methanol. $[\alpha]_D^{24}$ −68.8° (c 1.1, ethanol).

9-O-propionyl-3''-O-acetoxymethyl-SF-837 substance [in the general formula (II): $R_1$ = propionyl and $R_2$ = acetoxymethyl] is such a substance which does not substantially have the bitter taste and is an amorphous compound of a melting point of 104°–108°C. $[\alpha]_D^{23}$ −70.8° (c 1.0, ethanol).

9-O-acetyl-3''-O-propionyloxymethyl-SF-837-substance [in the general formula (II): $R_1$ = propionyl and $R_2$ = propionyloxymethyl] is such a substance which has little bitter taste and is a colorless crystalline compound of a melting point of 178°–179°C (sintered) after the recrystallization from 75% aqueous methanol. $[\alpha]_D^{24}$ −72.2° (c 1.0, ethanol).

9-O-propionyl-3''-O-propionyloxymethyl-SF-837 substance [in the general formula (II): $R_1$ = propionyl and $R_2$ = propionyloxymethyl] is such a substance which has little bitter taste and is a colorless amorphous compound of a melting point of 114°–116°C. $[\alpha]_D^{24}$ −72.5° (c 1.0, ethanol).

The antibacterial spectra of these new compounds 9-O-alkanoyl-3''-O-alkanoyloxymethyl-SF-837 substances are shown in Table 1 below, together with the antibacterial spectrum of the original SF-837 substance. The minimum inhibitory concentrations of these compounds to various microorganisms were determined according to a standard serial dilution method using Brain Heart Infusion broth as the incubation medium at 37°C, the estimation of the growth of the microorganisms being effected after 24 hours' incubation.

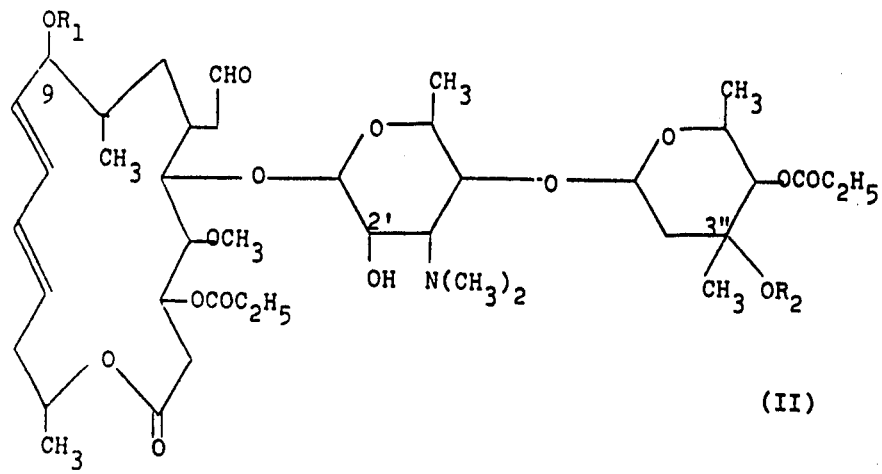

(II)

Table 1

| Microorganism tested | Minimum Inhibitory Concentrations (mcg/ml) | | | | |
|---|---|---|---|---|---|
| | 9-O-acetyl-3''-O-acetoxymethyl-SF-837 | 9-O-propionyl-3''-O-acetoxymethyl-SF-837 | 9-O-acetoxy-3''-O-propionyloxymethyl-SF-837 | 9-O-propionyl-3''-O-propionyloxymethyl-SF-837 | SF-837 (the free base) |
| Staphylococcus aureus 209P | 1.56 | 1.56 | 1.56 | 1.56 | 0.78 |
| Staphylococcus aureus Terajima | 3.13 | 3.13 | 3.13 | 3.13 | 1.56 |
| Staphylococcus aureus Smith | 1.56 | 3.13 | 1.56 | 1.56 | 0.19 |
| Staphylococcus albus 1200A | 1.56 | 1.56 | 1.56 | 3.13 | 0.78 |

Table 1-continued

| Microorganism tested | Minimum Inhibitory Concentrations (mcg/ml) | | | | |
|---|---|---|---|---|---|
| | 9-O-acetyl-3''-O-acetoxymethyl-SF-837 | 9-O-propionyl-3''-O-acetoxymethyl-SF-837 | 9-O-acetoxy-3''-O-propionyloxymethyl-SF-837 | 9-O-propionyl-3''-O-propionyloxymethyl-SF-837 | SF-837 (the free base) |
| Streptococcus faecalis ATCC 8043 | 1.56 | 1.56 | 1.56 | 3.13 | 1.56 |
| Streptococcus hemolyticus Cook | 0.19 | 0.19 | 0.19 | 1.56 | 0.09 |
| Streptococcus hemolyticus D-90 | 1.56 | 1.56 | 1.56 | 1.56 | 1.56 |
| Streptococcus pyogenes D-58 | 1.56 | 3.13 | 1.56 | 1.56 | 0.09 |
| Diplococcus pneumoniae Type I | 0.19 | 0.19 | 0.19 | 0.19 | 0.04 |
| Diplococcus pneumoniae Type III | 1.56 | 1.56 | 1.56 | 1.56 | 0.04 |
| Bacillus subtilis PCI 219 | 0.78 | 0.78 | 0.39 | 0.78 | 0.78 |
| Bacillus subtilis ATCC 6633 | 0.78 | 0.78 | 0.78 | 0.78 | 1.56 |
| Bacillus anthracis No.119 | 1.56 | 1.56 | 1.56 | 1.56 | 0.78 |
| Corynebacterium diphtheriae Type gravis | 0.19 | 0.19 | 0.19 | 0.19 | 0.19 |
| Corynebacterium diphtheriae Type intermedius | 0.19 | 0.19 | 0.19 | 0.19 | 0.19 |
| Sarcina lutea | 0.19 | 0.19 | 0.19 | 0.19 | 0.09 |

From the results of Table 1, it will be clear that the new compound of the general formula (II) according to this invention exhibits a high antibacterial activity to the Gram-negative and Gram-positive bacteria as much as that of the parent antibiotic, namely, the SF-837 substance (the free base) itself and also may be used as an antibacterial agent in a similar manner to the SF-837 substance. It has also been found that the new compound of the general formula (II) gives a higher curative effect than the original SF-837 substance (the free base) when it is administered orally to mice which have intraperitoneally been infected with Staphylococcus aureus.

The curative effect of the 9-O-alkanoyl-3''-O-alkanoyloxymethyl-SF-837 substances of the general formula (II) in the therapeutic treatment of Staphylococcus aureus Smith S-424 infections in mice was tested in the following way: Thus, an aqueous suspension of a pathogenic Staphylococcus aureus 209P in an aqueous solution of 5% gastric mucin was injected intraperitoneally to mice each at an inoculum size of 100 times higher than the $LD_{50}$ quantity of said strain for inoculation. The mice were classified into several groups each consisting of 10 mice. A dosage of 400 mg/kg, 200 mg/kg and 100 mg/kg of a test compound suspended in an aqueous solution of 2% gum arabic (0.5 ml) was then given orally to the infected mice immediately after the inoculation. The mice so treated were then usually raised for 7 days, and 7th day after the administration of the test compound, the number of the surviving mice in each group was counted. The test results obtained are shown in Table 2 below.

Table 2

| Test Compounds | Rate of Surviving Mice (in percentage) | | |
|---|---|---|---|
| | 400 mg/kg | 200 mg/kg | 100 mg/kg |
| (1) 9-O-acetyl-3''-O-acetoxymethyl-SF-837 | | | |
| (2) 9-O-propionyl-3''-O-acetoxymethyl-SF-837 | 100 | 56 | 33 |
| (3) 9-O-acetyl-3''-O-propionyloxymethyl-SF-837 | 100 | 100 | 67 |
| (4) 9-O-propionyl-3''-O-propionyloxymethyl-SF-837 | 100 | 56 | 33 |
| (5) SF-837 (free base) | 67 | 45 | 0 |

In order to estimate the acute toxicity of the new compound of the general formula (II), the compound was given intraperitoneally at a dosage of 3,000 mg/kg to several groups of mice each consisting of 3 mice. One week after the dosing, the rate of the sacrificed mice was counted and the results obtained are shown in Table 3 below.

Table 3

| Test compounds | Rate of the sacrificed mice (average) |
|---|---|
| 9-O-acetyl-3''-O-acetoxymethyl-SF-837 | 0/3 |
| 9-O-propionyl-3''-O-acetoxymethyl-SF-837 | 0/3 |
| 9-O-acetyl-3''-O-propionyloxymethyl-SF-837 | 0/3 |
| 9-O-propionyl-3''-O-propionyloxymethyl-SF-837 | 0/3 |
| SF-837 substance (the free base) (comparative) | 3/3 |

Moreover, the 9-O-alkanoyl-3''-O-alkanoyloxymethyl-SF-837 substances of the general formula (II) are found to have practically no bitter taste which is usually inherent to the macrolide antibiotics, so that the new compounds of this invention is advantageously suitable to be formulated as a liquid preparation which is intended to be given orally to infants. In view of all the above-mentioned micro-biological and biological properties of the 9-O-alkanoyl-3''-O-alkanoyloxymethyl-SF-837 substances of this invention, it will be clear that the 9-O-alkanoyl-3''-O-alkanoyloxymethyl-SF-837 substances have the significantly improved properties as the antibacterial agent, as compared to the original SF-837 substance. The new compound of the formula (II) of this invention may be formulated into an aqueous solution or suspension in a conventional pharmaceutical manner for oral administration and also for injection, and they may, of course, be made up into the other various formulations such as tablets, capsules, pulver and granules with aid of a known pharmaceutically acceptable carrier of vehicle such as starch, lactose, carcium carbonate and others.

According to a second aspect of this invention, there is provided a process for the production of a 9-O-alkanoyl-3''-O-alkanoyloxymethyl-SF-837 substance of the above-mentioned general formula (II), which comprises hydrolyzing selectively a 9,2'-di-O-alkanoyl-3''-O-alkanoyloxymethyl-SF-837 substance of the general formula (III):

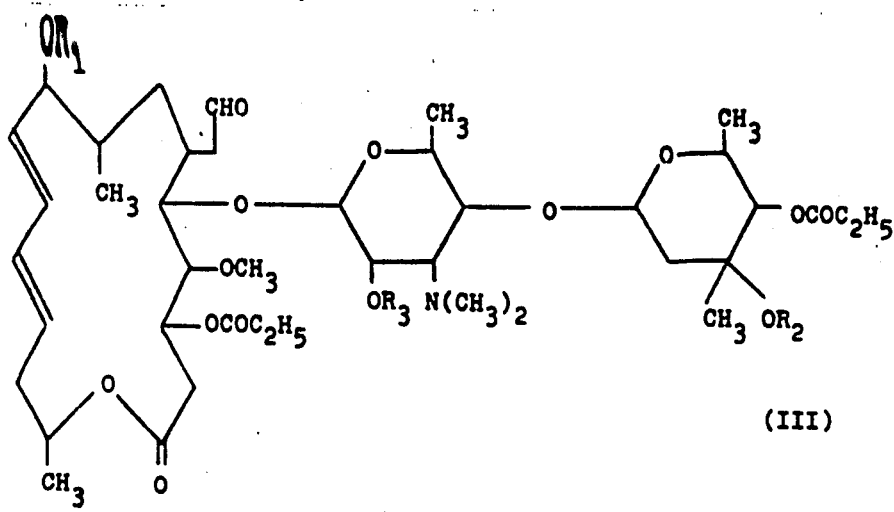

(III)

wherein $R_1$ is acetyl or propionyl, $R_2$ is acetoxymethyl or propionyloxymethyl and $R_3$ is acetyl or propionyl, by treating the latter compound with an aqueous alkanol or an aqueous acetone to produce the desired corresponding 9-O-alkanoyl-3''-O-alkanoyloxymethyl-SF-837 substance.

In the second aspect process of this invention, the selective hydrolysis of the 9,2'-di-O-alkanoyl-3''-O-alkanoyloxymethyl-SF-837 substance (III) into the desired 9-O-alkanoyl-3''-O-alkanoyloxymethyl-SF-837 substance (II) may be effected with preferential removal of the 2'-alkanoyl group, by dissolving the starting compound (III) in the aqueous medium such as an aqueous alkanol, preferably an alkanol of 1–4 carbon atoms containing a proportion of water, for example, aqueous methanol, aqueous ethanol, aqueous propanol, aqueous butanol and aqueous acetone, and then leaving the resulting solution to stand at a temperature of from ambient temperature to 100°C. When it is intended to effect the preferential removal of the 2'-acetyl group, the partial hydrolysis reaction may usually be completed in about 24 hours at ambient temperature. When it is intended to perform the preferential removal of the 2'-proprionyl group, the partial hydrolysis reaction may usually be completed in about 24 hours at an elevated temperature of e.g. 40°C. Addition of a small amount of a weak base such as triethylamine and sodium bicarbonate to the reaction medium for the hydrolysis reaction can accelerate the removal of the 2'-alkanoyl group. Such weak base may be added, for example, in one equivalent proportion to the alkanoic acid to be liberated from the 2'-position. The aqueous alkanol or acetone may suitably contain 10% to 30% by volume of water. The recovery of the desired compound (II) from the reaction mixture may conveniently be conducted, after evaporation of organic solvent, by extracting the reaction residue with an organic solvent such as benzene or ethyl acetate, washing the extracted solution of the desired product with water and then concentrating said solution by evaporation of the organic solvent to deposit the desired product.

The 9,2'-di-O-alkanoyl-3''-O-alkanoyloxymethyl-SF-837 substance of the general formula (III) which is used as the starting material in the first aspect process of this invention is itself the new compound and may be prepared by reacting the known 9,2'-di-O-acetyl- or 9,2'-di-O-propionyl-SF-837 substance (see the "Journal of Antibiotics" Vol. 24, pages 457 and 473, 1971) or the known 9-mono-O-acetyl- or 9-mono-O-propionyl-SF-837 substance (see British patent No. 1,358,114) with acetic anhydride or propionic anhydride and dimethylsulfoxide to form a 9,2'-di-O-alkanoyl-3''-O-thiomethoxymethyl-SF-837 substance of the following general formula (IV):

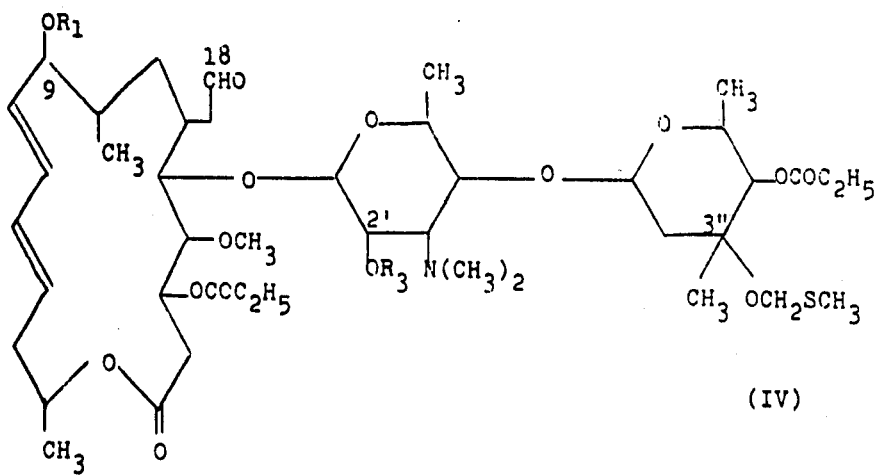

(IV)

wherein $R_1$ is acetyl or propionyl and $R_3$ is acetyl or propionyl, and then reacting this 9,2'-di-O-alkanoyl-3''-O-thiomethoxymethyl-SF-837 substance, with or without the isolation of this compound (IV), with acetic anhydride or propionic anhydride preferably in the presence of carbon tetrachloride to produce the 9,2'-di-O-alkanoyl-3''-O-acetoxymethyl- or 9,2'-di-O-alkanoyl-3''-O-propionyloxymethyl-SF-837 substance of the formula (III). The compound (IV) as isolated may be oxidised into its sulfoxide derivative by treating with 30% aqueous hydrogen peroxide, and this sulfoxide derivative (in which the thiomethoxymethyl group -CH$_2$SCH$_3$ in the compound (IV) has been converted into its sulfoxide type

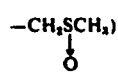

may also be reacted with acetic anhydride or propionic anhydride preferably in the presence of carbon tetrachloride to give the corresponding 9,2'-di-O-alkanoyl-3''-O-alkanoyloxymethyl-SF-837 substance of the formula (III). Moreover, the 3''-O-thiomethoxymethyl compound of the formula (IV) as isolated may partially be hydrolyzed by treating with an aqueous alkanol or acetone in the same manner as in the second aspect process of this invention to give the corresponding 9-O-alkanoyl-3''-O-thiomethoxymethyl-SF-837 substance. This 9-O-alkanoyl-3''-O-thiomethoxymethyl-SF-837 substance may also be oxidized into its sulfoxide derivative by treating with 30% aqueous hydrogen peroxide, and this sulfoxide derivative may be reacted with acetic or propionic anhydride preferably in the presence of carbon tetrachloride to form the corresponding 9-mono-O-alkanoyl-3''-O-alkanoyloxymethyl-SF-837 substance of the formula (II).

According to a third aspect of this invention, therefore, there is provided a process for the production of the 9-O-alkanoyl-3''-O-alkanoyloxymethyl-SF-837 substance of the above-mentioned general formula (II), which comprises the first step of replacing by acetoxy or propionyloxy the methylthio group of a 9,2'-di-O-alkanoyl- or 9-mono-O-alkanoyl-3''-O-thiomethoxymethyl-SF-837 substance of the general formula (V):

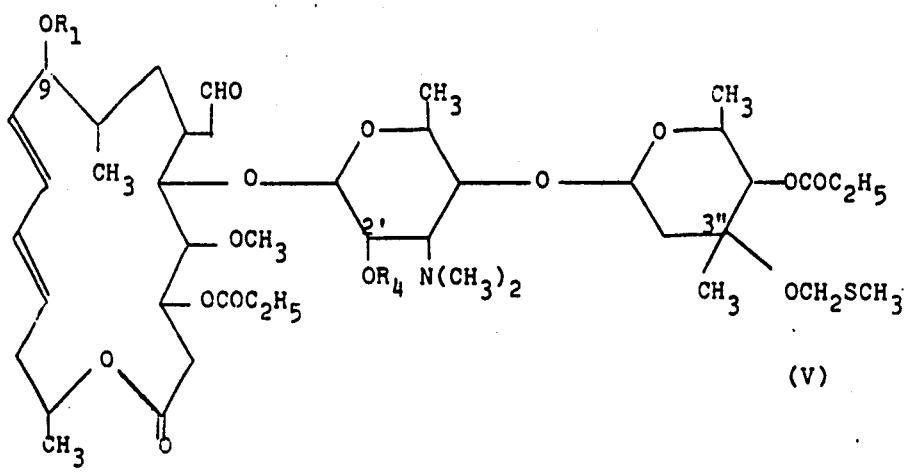

wherein $R_1$ is acetyl or propionyl and $R_4$ is hydrogen, acetyl or propionyl, or a sulfoxide derivative thereof by reacting with acetic anhydride or propionic anhydride, preferably in the presence of a small amount of dimethylsulfoxide, to produce the 9,2'-di-O-alkanoyl-3''-O-alkanoyloxymethyl-SF-837 substance of the general formula (III):

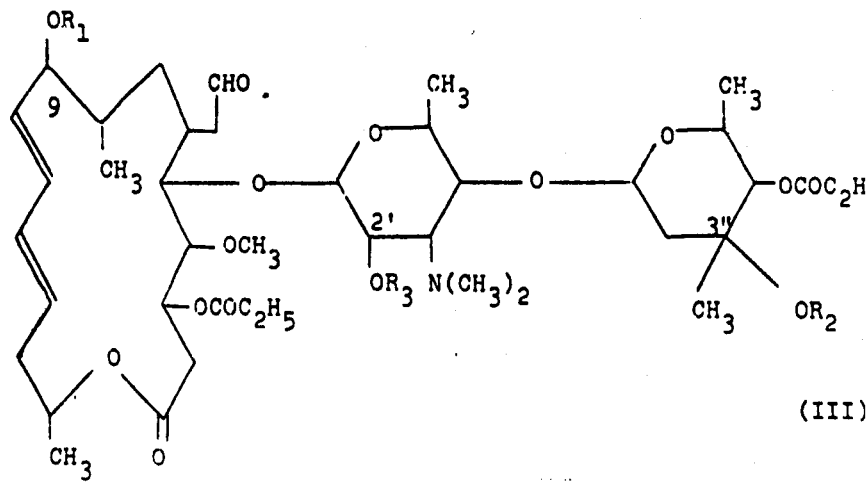

wherein R₁ is acetyl or propionyl, R₂ is acetoxymethyl or propionyloxymethyl and R₃ is acetyl or propionyl, and the second step of hydrolyzing selectively the 9,2'-di-O-alkanoyl-3''-O-alkanoyloxymethyl-SF-837 substance (III) by treating with an aqueous alkanol or an aqueous acetone to produce the desired corresponding 9-O-alkanoyl-3''-O-alkanoyloxymethyl-SF-837 substance.

In the third aspect process of this invention, the first, replacement-reaction step of reacting the 9,2'-di-O-alkanoyl- or 9-mono-O-alkanoyl-3''-O-thiomethoxymethyl-SF-837 substance (V) or its sulfoxide derivative with acetic or propionic anhydride may be carried out in an organic solvent which is inert to the replacement reaction, such as benzene, chloroform, carbon tetrachloride and dimethylsulfoxide. The use of pyridine as the solvent must be avoided, as it can hinder the desired replacement reaction. The replacement reaction may conveniently be carried out at ambient temperature or at a temperature of up to 80°C for a reaction time of 10 hours to 5 days. The reaction temperature may preferably be up to 55°C, as undesired side-reaction would take place significantly at a reaction temperature of more than 55°C. The desired replacement reaction of the first step may be promoted by providing the presence of a small amount of carbon tetrachloride and dimethylsulfoxide in the reaction medium or by using carbon tetrachloride as the reaction medium. The acetic anhydride or propionic anhydride which is used as the reagent in the first step of the third aspect process of this invention may preferably be present at least in an equi-molar proportion to the 9,2'-di-O-alkanoyl- or 9-mono-O-alkanoyl-3''-O-thiomethoxymethyl-SF-837 substance (V). When the third aspect process of this invention is carried out using for the starting compound the 9,2'-di-O-alkanoyl-3''-O-thiomethoxymethyl-SF-837 substance of the general formula (IV) which corresponds to such a form of the compound of the aforesaid formula (V) in which R₁ and R₄ each is acetyl or propionyl, it is possible, if desired, to prepare the starting compound of such form (IV) in situ in the reaction medium in which the first step of the third aspect process of this invention is to be performed. Thus, the 9,2'-di-O-alkanoyl-3''-O-thiomethoxymethyl-SF-837 substance of the formula (IV) which may be employed as one of the starting material (V) in the third aspect process of this invention may be prepared by introducing the 9,2'-di-O-acetyl- or 9,2'-di-O-propionyl- or 9-O-acetyl- or 9-O-propionyl-SF-837 substance with acetic anhydride or propionic anhydride and dimethylsulfoxide into and interacting these reagetns in the reaction medium in which the first step of the third aspect process of this invention takes place. In this case, it does not always need to isolate the compound (IV) so prepared from said reaction medium, before the first step of the third aspect process of this invention is commenced.

The process of preparing the compound of the form (IV) by reacting the 9,2'-di-O-alkanoyl- or 9-O-alkanoyl-SF-837 substance with acetic anhydride or propionic anhydride and dimethylsulfoxide may be conducted at a temperature of up to 50°C and preferably at 40°C for a reaction time of 1 to 7 days, in a large excess of dimethylsulfoxide which may equally be utilized as the reaction medium in which the reaction according to the first step of the third aspect process of this invention is carried out. Use or presence of carbon tetrachloride should be avoided in the process of preparing the compound of the form (IV), whereas addition of a small amount of pyridine to the reaction medium promotes the formation of the compound (IV). A part of the dimethylsulfoxide forming the reaction medium may, if desired, be replaced by an inert organic solvent such as benzene and toluene. In case an excess of acetic anhydride is provided in the reaction mixture during the process of preparing the compound (IV), the latter compound once formed will further react with another quantity of acetic anhydride present in said reaction mixture, involving the formation of the 9,2'-di-O-alkanoyl-3''-O-acetoxymethyl-SF-837 substance of the formula (III), so that the process of preparing the starting compound of the form (IV) and the reaction according to the first step of the third aspect process of this invention are then deemed to proceed concurrently in the same reaction system.

To recover the 9,2'-di-O-alkanoyl-3''-O-alkanoyloxymethyl-SF-837 substance (III) from the reaction mixture containing this compound which is resulted from the first step of the present process, the excess of the reagents and the reaction solvent may be removed out of the reaction mixture by distillation or evaporation, so that the compound (III) is left as the residue. For the recovery, it is rather convenient that the reaction mixture is poured into a large volume of ice-water containing sodium hydrogen carbonate in an amount sufficient to neutralize the acidity of the mixture, to extract the whole admixture with an organic solvent such as benzene, toluene or ethyl acetate and to dry and concentrate the resulting organic extract to dryness, leaving the desired intermediate compound (III) as the residue. The 9,2'-di-O-alkanoyl-3''-O-alkanoyloxymethyl-SF-837 substance (III) may, if desired or required, be purified by an usual chromatographic method or counter-current distribution method.

The 9,2'-di-O-alkanoyl-3''-O-alkanoyloxymethyl-SF-837 substance (III) isolated as above may subsequently be hydrolyzed selectively in the second step of the third aspect process of this invention which may be effected in the same manner as in the second aspect process of this invention by treating the compound (III) with an aqueous alkanol or aqueous acetone to give the desired compound of the general formula (II).

The present invention is now illustrated with reference to the following Examples to which the invention is not limited.

EXAMPLE 1

Production of 9-O-acetyl-3''-O-acetoxymethyl-SF-837 substance a. 9,2'-di-O-acetyl-SF-837 substance (5.0 g) which was free from pyridine as the impurity was dissolved in a mixture of 25 ml of acetic anhydride and 100 ml of dimethylsulfoxide, and the solution so obtained was allowed to stand at 28°C for 7 days. The reaction solution (mixture) was poured into a large volume of icewater containing sodium hydrogen carbonate, and the admixture was extracted twice with 200 ml portions of benzene. The benzene extracts were combined together and washed twice with water, dried over anhydrous sodium sulfate and then concentrated to dryness.

The residue was taken up into a small volume of benzene and the resulting solution was passed downward through a column of silica gel (2.8 cm × 1.8 cm) for chromatography. The silica gel column was eluated with benzene-acetone (10:1). The eluate was collected in 8 g fractions, and the fractions Nos. 11 to 18 were combined together and concentrated to dryness, giving 3.5 g of 9,2'-di-O-acetyl-3''-O-acetoxymethyl-SF-837 substances as an amorphous powder.

Melting point: 103-106°C
Molecular weight: 969
(determined by mass spectrometry)
Elemental analysis:
Calcd. for $C_{48}H_{75}NO_{18}$: C 59.43, H 7.79, N 1.44, O 31.33%
Found: C 59.15, H 7.58, N 1.52 b. The above product, 9,2'-di-O-acetyl-3''-O-acetoxymethyl-SF-837 substance (3.0 g) was dissolved in 100 ml of methanol containing 10% by volume of water, and the resulting solution was allowed to stand at ambient temperature overnight. The reaction solution was concentrated to dryness, affording 9-O-actyl-3''-O-actoxymethyl-SF-substance as an amorphous powder in a substantially quantitative yield. Melting point: 106°-111°C.

This product showed a melting point of 174°-176°C (sintered) after it was crystallized as a colorless crystalline substance from 75% aqueous methanol.

$[\alpha]_D^{24}$ −68.8° (c 1.1, ethanol).
Molecular weight: 927
(determined by mass spectrometry)
Elemental analysis:
Calcd. for $C_{46}H_{73}NO_{18}$: C 59.53, H 7.93, N 1.51, O 31.03%
Found: C 59.71, H 7.68, N 1.72%

EXAMPLE 2

Production of 9-O-acetyl-3''-O-acetoxymethyl-SF-837 substance a. 9,2'-di-O-acetyl-SF-837 substance (3.0 g) which was free from pyridine was dissolved in a mixture of 15 ml of acetic anhydride, 60 ml of dimethylsulfoxide and 7.5 ml of carbon tetrachloride, and the solution so obtained was allowed to stand at 28°C for 6 days. The reaction solution was subsequently processed in the same manner as in Example 1(a), giving 2.1 g of 9,2'-di-O-acetyl-3''-O-acetoxymethyl-SF-837 substance.

b. The 9,2'-di-O-acetyl-3''-O-acetoxymethyl-SF-837 substance (4.0 g) was taken up into 150 ml of 90% aqueous ethanol, and the solution was allowed at ambient temperature overnight. Concentration of the reaction solution to dryness gave 9-O-acetyl-3''-O-acetoxymethyl-SF-837 substance in a substantially quantitative yield.

EXAMPLE 3

Production of 9-O-propionyl-3''-O-acetoxymethyl-SF-837 substance a. The process of Example 1(a) was repeated using 1 g of 9,2'-di-O-propionyl-SF-837 substance instead of the 9,2'-di-O-acetyl-SF-837 substance. 9,2'-di-O-propionyl-3''-O-acetoxymethyl-SF-837 substance was obtained as an amorphous product in a yield of 540 mg.

Melting point: 101-105°C
Molecular weight: 997
(determined by mass spectrometry)
Elemental analysis:
Calcd. for $C_{50}H_{79}NO_{18}$: C 60.16, H 7.98, N 1.40, O 30.46%
Found: C 60.32, H 7.59, N 1.18% b. The 9,2'-di-O-propionyl-3''-O-acetoxymethyl-SF-837 substance (500 mg) was taken up into 50 ml of 90% aqueous methanol, and the resulting solution was allowed to stand at 40°C overnight. The reaction mixture was then processed similarly to Example 1(b), affording an amorphous powder of 9-O-propionyl-3''-O-acetoxymethyl-SF-837 substance in a substantially quantitative yield.

Melting Point: 104-108°C
Molecular weight: 941
(determined by mass spectrometry)
Elemental analysis:
Calcd. for $C_{47}H_{75}NO_{18}$: C 59.52, H 8.02, N 1.49, O 30.57%
Found: C 59.71, H 8.25, N 1.17%

EXAMPLE 4

Production of 9-O-acetyl-3''-O-acetoxymethyl-SF-837 substance a. The process of Example 1(a) was repeated using a 1 g of 9-O-acetyl-SF-837 substance in place of the 9,2'-di-O-acetyl-SF-837 substance. 9,2'-di-O-acetyl-3''-O-acetoxymethyl-SF-837 substance was obtained in a yield of 780 mg.

b. The 9,2'-di-O-acetyl-3''-O-acetoxymethyl-SF-837 substance (700 mg) was taken up into 50 ml of 90% aqueous acetone, and the solution obtained was left to stand at 28°C overnight. The reaction mixture was concentrated to dryness to give the 9-acetyl-3''-O-acetoxymethyl-SF-837 substance in a substantially quantitative yield.

EXAMPLE 5

Preparation of 9-O-propionyl-2'-O-acetyl-3''-O-thiomethoxymethyl-SF-837 substance a. 9-O-propionyl-SF-837 substance (15 g) was dissolved in a mixture of 10 ml of acetic anhydride and 50 ml of pyridine, and the resulting solution was allowed to stand at ambient temperature for 4 hours. The reaction solution was poured into 300 ml of water containing 100 g of ice, and the admixture so obtained was then neutralized by addition of sodium hydrogen carbonate and subsequently extracted three times with 200 ml portions of benzene. The benzene extracts were combined together and dried over anhydrous sodium sulfate. The solution in benzene was concentrated to dryness and the residue was taken up into 10 ml of carbon tetrachloride. Cooling of the resulting solution gave 13 g of 9-O-propionyl-2'-O-acetyl-SF-837 substance as a crystalline product.

Melting point: 118-122°C
Molecular weight: 911
(according to mass spectrometry)
Elemental analysis:
Calcd. for $C_{46}H_{73}NO_{17}$: C 60.58, H 8.07, N 1.54, O 29.82%
Found: C 60.37, H 7.98, N 1.45% b. The 9-O-propionyl-2'-O-acetyl-SF-837 substance (12 g) was dissolved in a mixture of 25 ml of acetic anhydride and 100 ml of dimethylsulfoxide, and the solution so obtained was allowed to stand at 37°C for 40 hours. The reaction solution was concentrated under a reduced pressure and at a temperature of 50°C or less, and the residue was extracted three times with 200 ml portions of hot hexane. The hexane extracts were combined together and was left in a cold place, crystallizing out 11 g of 9-O-propionyl-2'-O-acetyl-3''-O-thiomethoxymethyl-SF-837 substance.

| | |
|---|---|
| Melting point: | 170–176°C |
| Molecular weight: (according to mass spectrometry) | 971 |
| Elemental analysis: | |
| Calcd. for $C_{48}H_{77}NO_{17}S$: | C 59.30, H 7.98, N 1.44, O 27.98, S 3.30% |
| Found: | C 59.28, H 7.95, N 1.44, S 3.01% |

EXAMPLE 6

Production of 9-O-propionyl-3''-O-acetoxymethyl-SF-837 substance a. The product of Example 5(b), that is, the 9-O-propionyl-2'-O-acetyl-3''-O-thiomethoxymethyl-SF-837 substance (10 g) was taken up into 320 ml of carbon tetrachloride, and the solution so obtained was then admixed with 80 ml of acetic anhydride and 2 ml of dimethylsulfoxide. The resulting admixture was allowed to stand at 50°C for 10 hours. The reaction mixture was concentrated under a reduced pressure at a temperature of 45°C or less, then admixed with 20 ml of toluene and again concentrated under a reduced pressure. The resulting syrup was dissolved in a small volume of mixture of benzene-acetone (13:1 by volume) and passed downward through a column of silica gel (6 cm in diameter by 27 cm in height). The silica gel column was then eluted with the benzene-acetone (13:1) mixture, and the eluate was collected in 10 g fractions. The fraction Nos. 65 to 180 were combined together and concentrated, giving 7.5 g of 9-O-propionyl-2'-O-acetyl-3''-O-acetoxymethyl-SF-837 substance as an amorphous powder.

| | |
|---|---|
| Melting point: | 104–107°C |
| Molecular weight: (according to mass spectrometry) | 983 |
| Elemental analysis: | |
| Calcd. for $C_{49}H_{77}NO_{19}$: | C 59.80, H 7.89, N 1.42, O 30.89% |
| Found: | C 59.54, H 7.58, N 1.28% | b. The 9-O-propionyl-2'-O-acetyl-3''-acetoxymethyl-SF-837 substance (5 g) was taken up into 100 ml of 90% aqueous methanol, and the resulting solution was allowed to stand at 40°C for 20 hours, yielding 4.7 g of the 9-O-propionyl-3''-O-acetoxymethyl-SF-837 substance which was confirmed to be identical to the product of the process of Example 3(b).

EXAMPLE 7

Preparation of 9,2'-di-O-acetyl-3''-O-thiomethoxymethyl-SF-837 substance and 9-O-acetyl-3''-O-thiomethoxymethyl-SF-837 substance a. 9,2'-di-O-acetyl-SF-837 substance (1.0 g) was dissolved in a mixture of 3 ml of acetic anhydride and 30 ml of dimethylsulfoxide, and the resulting solution was allowed to stand for 4 days at ambient temperature. The reaction solution was admixed with 100 ml of benzene and the mixture was washed three times with water and the benzene phase was separated out from the aqueous phase. The benzene phase was concentrated to dryness. The aqueous phase was adjusted to pH 8 by addition of sodium hydrogen carbonate and then extracted with benzene, and the resulting benzene extract was concentrated to dryness.

The residue of the benzene phase first separated out was taken up into a small volume of benzene and the benzene solution so obtained was passed downward through a column of silica gel (2.7 cm × 16 cm) for chromatography. The silica gel column was eluted with a mixture of benzene-acetone (9:1 by volume), and the eluate was collected in 8 g fractions. Fraction Nos. 11 to 14 were combined together and concentrated to dryness, giving 662 mg of 9,2'-di-O-acetyl-3''-O-thiomethoxymethyl-SF-837 substance as an amorphous powder. The residue of the benzene extract which was obtained from the extraction of the aqueous phase with benzene was treated in a similar way to give 60 mg of the second crop.

| | |
|---|---|
| Melting point: | 100–104°C |
| Molecular weight: (according to mass spectrometry) | 957 |
| Elemental analysis: | |
| Calcd. for $C_{47}H_{75}NO_{17}S$: | C 58.91, H 7.89, N 1.46, S 3.35% |
| Found: | C 58.70, H 7.80, N 1.20, S 3.00% | b. The 9,2'-di-O-acetyl-3''-O-thiomethoxymethyl-SF-837 substance (725 mg) was taken up into dry methanol (30 ml), and the solution so obtained was admixed with 10% by weight of water and then allowed to stand at ambient temperature overnight. The reaction mixture was poured into a large amount of ice-water, which was then adjusted to pH 8 by addition of sodium hydrogen carbonate. The mixture was extracted with benzene, and the benzene extract was concentrated to dryness, affording 547 mg of an amorphous powder of 9-O-acetyl-3''-O-thiomethoxymethyl-SF-837 substance.

| | |
|---|---|
| Melting point: | 119–124°C |
| Molecular weight: (according to mass spectrometry) | 915 |
| Elemental analysis: | |
| Calcd. for $C_{45}H_{73}NO_{16}S$: | C 59.00, H 8.03, N 1.53, S 3.50% |
| Found: | C 58.85, H 7.98, N 1.40, S 3.30% |

EXAMPLE 8

Production of 9-O-acetyl-3''-O-acetoxymethyl-SF-837 substance a. The product of the Example 7(a), that is, the 9,2'-di-O-acetyl-3''-O-thiomethoxymethyl-SF-837 substance (10 g) was taken up into a mixture of 300 ml of carbon tetrachloride, 80 ml of acetic anhydride and 1.5 ml of dimethylsulfoxide, and the solution so obtained was allowed to stand at 28°C for 35 hours. The reaction solution was then processed in the same manner as in Example 7(a), affording 8.0 g of 9,2'-di-O-acetyl-3''-O-acetoxymethyl-SF-837 substance which was found to be identical to the product of Example 1(a).

b. The product of the above Example 8(a) was treated in the same manner as in Example 1(b), yielding the 9-O-acetyl-3''-O-acetoxymethyl-SF-837 substance.

EXAMPLE 9

Production of 9-O-acetyl-3''-O-acetoxymethyl-SF-837 substance a. The product of Example 7(b), namely the 9-O-acetyl-3''-O-thiomethoxymethyl-SF-837 substance (500 mg) was dissolved in a mixture of 20 ml of carbon tetrachloride and 8 ml of acetic anhydride, and the resulting solution was allowed to stand at 28°C for 5 days. The reaction solution was concentrated to dryness and the residue was taken up into a small volume of a mixture of benzene-acetone (10:1 by volume) and then chromatographed on a silica gel column (1.5 cm × 5 cm) using the benzene-acetone mixture (10:1 by volume) as the development solvent. 9,2'-O-acetyl-3''-O-acetoxymethyl-SF-837 substance was obtained. Yield 290 mg.

b. This product was treated in the same manner as in Example 1(b) except that the 90% aqueous methanol was replaced by 90% aqueous ethanol. 9-O-acetyl-3''-O-acetoxymethyl-SF-837 substance was obtained. Yield 245 mg.

EXAMPLE 10

Preparation of 9-O-propionyl-3''-O-thiomethoxymethyl-SF-837 substance a. The process of Example 7(a) was repeated using 1 g of 9,2'-di-O-propionyl-SF-837 substance in place of the 9,2'-di-O-acetyl-SF-837 substance. 9,2'-di-O-propionyl-3''-O-thiomethoxymethyl-SF-837 substance was obtained in a yield of 500 mg as amorphous powder.

| Melting point: | 115–120°C |
|---|---|
| Elemental analysis: | |
| Calcd. for $C_{46}H_{75}NO_{17}S$: | C 59.67, H 8.07, N 1.42, S 3.25% |
| Found: | C 59.50, H 8.00, N 1.26, S 3.10% | b. The 9,2'-di-O-propionyl-3''-O-thiomethoxymethyl-SF-837 substance (500 mg) was dissolved in 50 ml of methanol, to which was then added 5 ml of water. The mixture was allowed to stand at 40°C for 1 day. The reaction mixture was then processed in the same manner as in Example 7(b), yielding 400 mg of 9-O-propionyl-3''-O-thiomethoxymethyl-SF-837 substance as amorphous powder.

| Melting point: | 115–120°C |
|---|---|
| Elemental analysis: | |
| Calcd. for $C_{46}H_{75}NO_{16}S$: | C 59.40, H 8.13, N 1.51, S 3.45% |
| Found: | C 59.40, H 8.00, N 1.48, S 3.11% |

EXAMPLE 11

Production of 9-O-propionyl-3''-O-acetoxymethyl-SF-837 substance a. The product of Example 10(b), namely the 9-O-propionyl-3''-O-thiomethoxymethyl-SF-837 substance (420 mg) was dissolved in a mixture of 20 ml of carbon tetrachloride and 8 ml of acetic anhydride and then processed in the same manner as in Example 9(a), giving 270 mg of 9-O-propionyl-2'-O-acetyl-3''-O-acetoxymethyl-SF-837 substance which was found to be identical to the product of Example 6(a).

b. This product was treated in the same manner as in Example 6(b), affording the 9-O-propionyl-3''-O-acetoxymethyl-SF-837 substance.

EXAMPLE 12

Preparation of 9-O-acetyl-3''-O-thiomethoxy-methyl-SF-837 substance-sulfoxide

The product of Example 7(b), namely the 9-O-acetyl-3''-O-thiomethoxymethyl-SF-837 substance (250 mg) was dissolved in 30 ml of methanol, to which was added 0.5 ml of 30% aqueous hydrogen peroxide. The mixture was allowed to stand at ambient temperature for 4 hours and then manganese dioxide was added to the mixture to decompose the excess of hydrogen peroxide. The admixture was then filtered and the filtrate was concentrated to dryness. 9-O-acetyl-3''-O-thiomethoxymethyl-SF-837 substance-sulfoxide was obtained as a colorless amorphous powder in a substantially quantitative yield. This substance was positive to the reaction with sodium iodide and hydrochloric acid.

| Melting point: | 126–133°C (decomposed) |
|---|---|
| Molecular weight: | 931 |
| (according to mass spectrometry) | |
| Elemental analysis: | |
| Calcd. for $C_{45}H_{73}NO_{17}S$: | C 57.98, H 7.89, N 1.50, O 29.18, S 3.44% |
| Found: | C 58.15, H 7.78, N 1.62, S 3.19% |

EXAMPLE 13

Preparation of 9-O-propionyl-3''-O-thiomethoxymethyl-SF-837 substance-sulfoxide.

The product of Example 10(b), namely the 9-O-propionyl-3''-O-thiomethoxymethyl-SF-837 substance (270 mg) was treated with 30% aqueous hydrogen peroxide in the same manner as in Example 12, giving 9-O-propionyl-3''-O-thiomethoxymethyl-SF-837 substance-sulfoxide as an amorphous powder in a substantially quantitative yield.

| Melting point: | 105–115°C (decomposed with foaming) |
|---|---|
| Molecular weight: | 945 |
| (according to mass spectrometry) | |
| Elemental analysis: | |
| Calcd. for $C_{46}H_{75}NO_{17}S$: | C 58.39, H 7.99, N 1.48, O 28.75, S 3.38% |
| Found: | C 58.51, H 8.16, N 1.29, S 3.32% |

EXAMPLE 14

Production of 9-O-acetyl-3''-O-acetoxymethyl-SF-837 substance a. The product of Example 12, namely the 9-O-acetyl-3''-O-thiomethoxymethyl-SF-837 substance-sulfoxide (120 mg) was dissolved in 6 ml of carbon tetrachloride, and the resulting solution was admixed with 1.5 ml of acetic anhydride. The admixture was allowed to stand at 28°C for 70 hours. The reaction solution so obtained was concentrated to dryness. The residue was taken up into a small volume of a mixed solvent of benzene-acetone (10:1 by volume) and the solution so obtained was passed downward through a column of silica gel (1.5 cm × 5 cm) for chromatography. The silica gel column was then eluted with the mixed solvent of benzene-acetone (10:1 by volume). The eluate was collected in 2 g fractions, and the fractions Nos. 15 to 23 were combined together and concentrated, affording 65 mg of 9,2'-di-O-acetyl-3''-O-acetoxymethyl-SF-837 substance which was found to be identical to the product of Example 1(a).

b. This product was treated in the same manner as in Example 1(b) for the partial hydrolysis to give 9-O-acetyl-3''-O-acetoxymethyl-SF-837 substance in a substantially quantitative yield.

EXAMPLE 15

Production of 9-O-propionyl-3''-O-acetoxymethyl SF-837 substance a. The product of Example 13, namely the 9-O-propionyl-3''-O-thiomethoxymethyl-SF-837 substance sulfoxide (130 mg) was treated with acetic anhydride and carbon tetrachloride in the same manner as in Example 14(a), giving 85 mg of 9-O-propionyl-2'-O acetyl-3''-O-acetoxymethyl-SF-837 substance which was found to be identical to the product of Example 6(a).

b. This product was partially hydrolyzed by treating with 90% aqueous methanol in the same manner as in Example 6(b). 9-O-propionyl-3''-O-acetoxymethyl-SF-837 substance was obtained in a substantially quantitative yield.

EXAMPLE 16

Production of 9-O-acetyl-3''-O-propionyloxymethyl-SF-837 substance a. The process of Example 8(a) was repeated using 80 ml of propionic anhydride in place of the acetic anhydride. 9,2'-di-O-acetyl-3''-O-propionyloxymethyl-SF-837 substance was afforded in a yield of 6.5 g.

| | |
|---|---|
| Melting point: | 108–111°C |
| Molecular weight: (according to mass spectrometry) | 983 |
| Elemental analysis: | |
| Calcd. for $C_{48}H_{77}NO_{18}$: | C 59.80, H 7.89, N 1.42, O 30.89% |
| Found: | C 59.57, H 7.98, N 1.28% | b. The product of Example 16(a), namely the 9,2'-di-O-acetyl-3''-O-propionyloxymethyl-SF-837 substance (5 g) was treated with 90% aqueous methanol in the same manner as in Example 1(b), affording 9-O-acetyl-3''-O-propionyloxymethyl-SF-837 substance in a substantially quantitative yield. This product was recrystallized from 75% aqueous methanol and obtained in the form of a colorless crystalline product of mp. 178°–179°C (sintered).

| | |
|---|---|
| $[\alpha]_D^{24}$ −72.2° (c 1.0, ethanol). | |
| Molecular weight: (according to mass spectrometry) | 941 |
| Elemental analysis: | |
| Calcd. for $C_{47}H_{75}NO_{18}$: | C 59.52, H 8.02, N 1.49, O 30.57% |
| Found: | C 59.28, H 8.35, N 1.25% |

EXAMPLE 17

Production of 9-O-propionyl-3''-O-propionyloxymethyl-SF-837 substance a. The product of Example 10(a), namely the 9,2'-di-O-propionyl-3''-O-thiomethoxymethyl-SF-837 substance (10 g) was reacted with propionic anhydride in the same manner as in Example 8(a) except that 80 ml of acetic anhydride was replaced by 80 ml of propionic anhydride. 9,2'-di-O-propionyl-3''-O-propionyloxymethyl-SF-837 substance was obtained in a yield of 7 g. Melting point 116°–119°C.

b. The product of the Example 17(a) was treated with 90% aqueous methanol in the same manner as in Example 1(b), affording 9-O-propionyl-3''-O-propionyloxymethyl-SF-837 substance in a substantially quantitative yield.

| | |
|---|---|
| Melting point: | 114–116°C |
| Molecular weight: (according to mass spectrometry) | 955 |
| Elemental analysis: | |
| Calcd. for $C_{48}H_{77}NO_{18}$: | C 60.30, H 8.12, N 1.47, O 30.12% |
| Found: | C 60.02, H 8.31, N 1.28% |

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope of this invention, can make various change and modifications of this invention to adapt it to various usage conditions.

What we claim is:

1. A 9-O-alkanoyl-3''-O-alkanoyloxymethyl-SF-837 substance compound selected from the group consisting of 9-O-acetyl-3''-O-acetoxymethyl-SF-837 substance, 9-O-propionyl-3''-O-acetoxymethyl-SF-837 substance, 9-O-acetyl-3''-O-propionyloxymethyl-SF-837 substance and 9-O-propionyl-3''-O-propionyloxymethyl-SF-837 substance.

2. A compound as claimed in claim 1 which is 9-O-acetyl-3''-O-acetoxymethyl-SF-837 substance.

3. A compound as claimed in claim 1 which is 9-O-propionyl-3''-O-acetoxymethyl-SF-837 substance.

4. A compound as claimed in claim 1 which is 9-O-acetyl-3''-O-propionyloxymethyl-SF-837 substance.

5. A compound as claimed in claim 1 which is 9-O-propionyl-3''-O-propionyloxymethyl-SF-837 substance.

6. A process for the production of a 9-O-alkanoyl-3''-O-alkanoyloxymethyl-SF-837 substance as claimed in claim 1, which comprises the first step of reacting a 9,2'-di-O-alkanoyl- or 9-mono-O-alkanoyl-3''-O-thiomethoxymethyl-SF-837 substance of the general formula (V):

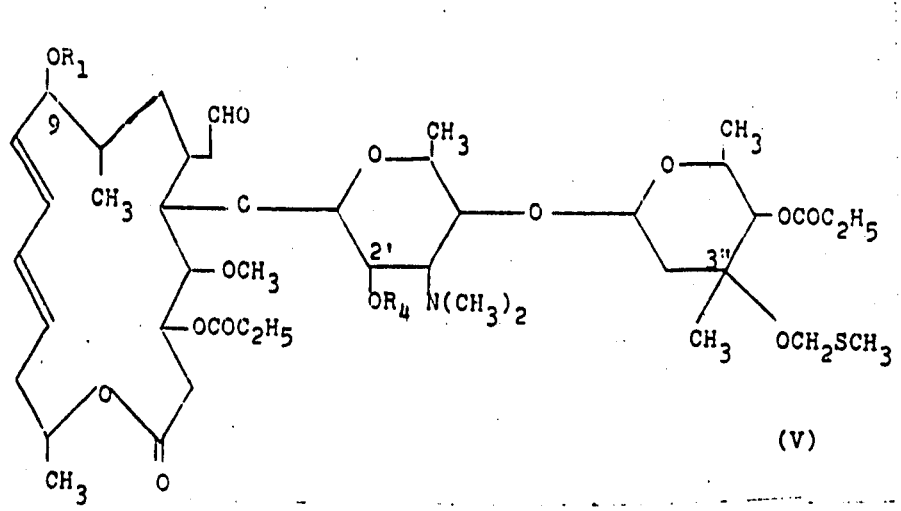

(V)

wherein $R_1$ is acetyl or propionyl and $R_4$ is hydrogen, acetyl or propionyl, or a sulfoxide derivative thereof, with acetic anhydride or propionic anhydride to produce the 9,2'-di-O-alkanoyl-3''-O-alkanoyloxymethyl-SF-837 substance of the general formula (III):

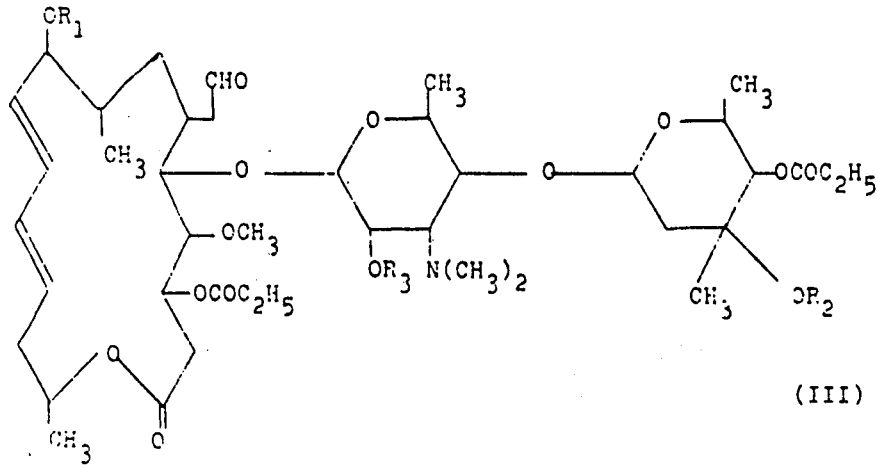

(III)

wherein $R_1$ is acetyl or propionyl, $R_2$ is acetoxymethyl or propionyloxymethyl and $R_3$ is acetyl or propionyl, and the second step of hydrolyzing selectively the 9,2'-di-O-alkanoyl-3''-O-alkanoyloxymethyl-SF-837 substance (III) by treating this compound with an aqueous alkanol or an aqueous acetone to produce the desired 9-O-alkanoyl-3''-O-alkanoyloxymethyl-SF-837 substance.

7. A process as claimed in claim 6 in which the reaction of the first step is carried out at a temperature of from ambient temperature to 50°C for 5 to 7 days.

8. A process as claimed in claim 6 in which the reaction of the first step is carried out in an inert solvent selected from dimethylsulfoxide, benzene, chloroform and carbon tetrachloride.

9. A process as claimed in claim 6 in which the reaction of the first step is carried out in the presence of carbon tetrachloride in addition to the reaction solvent.

10. A process as claimed in claim 6 in which the reaction of the first step is carried out concurrently with the process of preparing the 9,2'-di-O-alkanoyl-3''-O-thiomethoxymethyl-SF-837 substance of the formula (IV), in such a manner that the 9,2'-di-O-acetyl-, 9,2'-di-O-propionyl-, 9-O-acetyl- or 9-O-propionyl-SF-837 substance is reacted with acetic anhydride and dimethylsulfoxide in the presence of an excess of acetic anhydride and in a reaction medium consisting of the excess dimethylsulfoxide, benzene, chloroform or carbon tetrachloride or a mixture thereof at a temperature of from ambient temperature to 50°C for 1 to 7 days, without isolating the 9,2'-di-O-alkanoyl-3''-O-thiomethoxymethyl-SF-837 substance.

11. A process as claimed in claim 6 in which the 9,2'-di-O-alkanoyl-3''-O-alkanoyloxymethyl-SF-837 substance produced is isolated from the reaction mixture resulted from the first step and is then treated with an aqueous alkanol or aqueous acetone in the second, hydrolysis step of the process.

12. A 9,2'-di-O-alkanoyl-3''-O-alkanoyloxymethyl-SF-837 substance of the general formula (III):

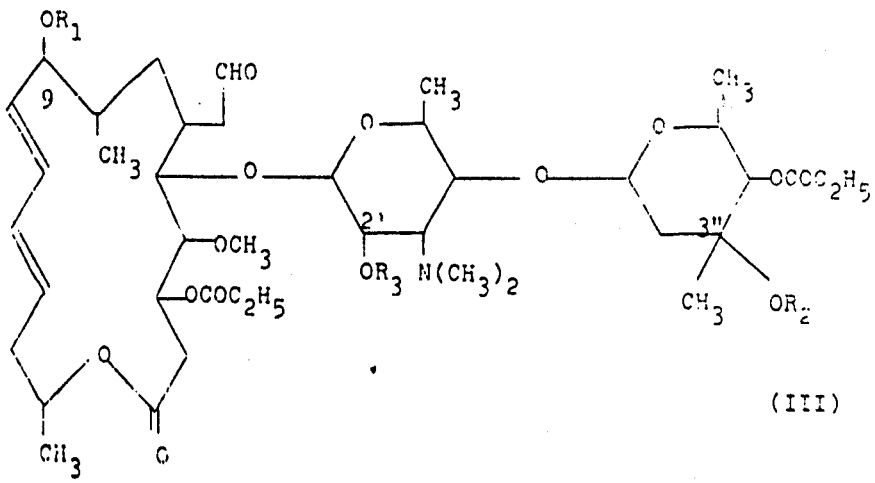

(III)

wherein $R_1$ is acetyl or propionyl, $R_2$ is acetoxymethyl or propionyloxymethyl, and $R_3$ is acetyl or propionyl.

* * * * *